United States Patent [19]

Su et al.

[11] Patent Number: 5,286,267
[45] Date of Patent: Feb. 15, 1994

[54] POLYETHER HYDROXYETHYLAMINOETHYL OXALAMIDE MOTOR FUEL DETERGENT ADDITIVES

[75] Inventors: Wei-Yang Su, Austin, Tex.; Sheldon Herbstman, New City, N.Y.; Robert L. Zimmerman; Michael Cuscurida, both of Austin, Tex.

[73] Assignee: Texaco Inc., White Plains, N.Y.

[21] Appl. No.: 993,798

[22] Filed: Dec. 21, 1992

[51] Int. Cl.$^5$ .................. C10L 1/22; C07C 233/00
[52] U.S. Cl. ........................... 44/419; 564/157
[58] Field of Search ..................... 44/419; 564/157

[56] References Cited

U.S. PATENT DOCUMENTS

| | | | |
|---|---|---|---|
| 4,234,321 | 11/1980 | Lilburn | 44/387 |
| 4,357,158 | 11/1982 | Graiff | 44/432 |
| 4,581,040 | 4/1986 | Sung et al. | 44/407 |
| 4,604,103 | 8/1986 | Campbell | 44/433 |
| 4,631,069 | 12/1986 | Sung | 44/407 |
| 4,643,738 | 2/1987 | Sung et al. | 44/407 |
| 4,659,336 | 4/1987 | Sung et al. | 44/407 |
| 4,659,337 | 4/1987 | Sung | 44/407 |
| 4,747,851 | 5/1988 | Sung et al. | 44/433 |

*Primary Examiner*—Jerry D. Johnson
*Attorney, Agent, or Firm*—George J. Darsa; James J. O'Louglin; Vincent A. Mallare

[57] ABSTRACT

The present invention provides a novel class of compounds, useful as gasoline detergent additives, which is a polyether hydroxyethylaminoethyl oxalamide represented by the formula

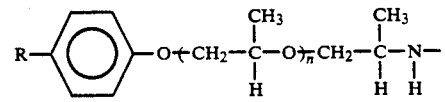
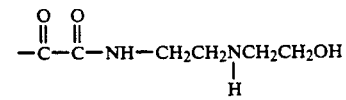

where R is a ($C_5$-$C_{25}$) alkyl group and $n$ is an integer between about 5 and about 20.

7 Claims, No Drawings

POLYETHER HYDROXYETHYLAMINOETHYL OXALAMIDE MOTOR FUEL DETERGENT ADDITIVES

BACKGROUND OF THE INVENTION

This invention is related to gasoline engine cleaners and detergents, and more particularly to gasoline intake valve deposit (IVD) inhibitor additives, i.e., agents which assist in preventing and removing deposits from intake valves and related parts of a gasoline combustion engine.

The combustion of a hydrocarbon motor fuel in an internal combustion engine generally results in the formation and accumulation of deposits on various parts of the combustion chamber as well as in the fuel intake and on the exhaust systems of the engine. The presence of deposits in the combustion chamber seriously reduces the operating efficiency of the engine. First, deposit accumulation within the combustion chamber inhibits heat transfer between the chamber and the engine cooling system. This leads to higher temperatures within the combustion chamber, resulting in increases in the end gas temperature of the incoming charge. Consequently, end gas auto-ignition occurs causing engine knock. In addition, the accumulation of deposits within the combustion chamber reduces the volume of the combustion zone, causing a higher than design compression ratio in the engine. This, in turn, can also lead to engine knocking. A knocking engine does not effectively utilize the energy of combustion. Moreover, a prolonged period of engine knocking can cause stress fatigue and wear in pistons, connecting rods, bearings and cam rods of the engine. The phenomenon noted is characteristic of gasoline powered internal combustion engines. It may be overcome by employing a higher octane gasoline which resists knocking for powering the engine. This need for higher octane gasoline as mileage accumulates has become known as the engine octane requirement increase (ORI) phenomenon. It is particularly advantageous if engine ORI can be substantially reduced or eliminated by preventing or modifying deposit formation in the combustion chambers of the engine.

Another problem common to internal combustion engines is the formation of intake valve deposits, which is an especially serious problem. Intake valve deposits interfere with valve closing and eventually result in poor fuel economy. Such deposits interfere with valve motion and valve sealing cause valve sticking, and, in addition, reduce volumetric efficiency of the engine and limit maximum power. Valve deposits are produced from the combustion of thermally and oxidatively unstable fuel or lubricating oil oxidation products. The hard carbonaceous deposits produced collect in the tubes and runners that are part of the exhaust gas recirculation (EGR) flow. These deposits are believed to be formed from exhaust particles which are subjected to rapid cooling while mixing with the air-fuel mixture. Reduced EGR flow can result in engine knock and in increased NOx emissions. It would therefore be desirable to provide a motor fuel composition which minimizes or overcomes the formation of intake valve deposits and subsequent valve sticking problems.

There are additives on the market which assist in the removal of deposits, particularly on the intake valves, such as OGA-472 TM, a product manufactured and sold by the Oronite Company of Wilmington, Del. These additives lack sufficient deposit cleanup activity, however, and their efficacy can be improved upon. In addition, polyisobutylene (PIB) based detergents tend to cause octane requirement increase.

Thus, it is an object of the present invention to provide a gasoline additive which will effectively remove deposits from, and prevent the formation of deposits on, the intake valves of a gasoline spark ignition engine. Another object of the present invention is to provide a gasoline additive which will perform this function without contributing to the buildup of combustion chamber deposits and, therefore, without causing octane requirement increase.

DISCLOSURE STATEMENT

U.S. Pat. No. 4,747,851 discloses a novel polyoxyalkylene diamine compound of the formula:

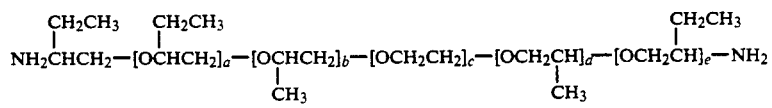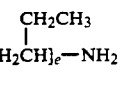

Where c has a value from about 5-150, b+d has a value from about 5-150, and a+e has a value from about 2-12. Motor fuel compositions comprising the novel polyoxyalkylene diamine, alone or in combination with a polymer/copolymer additive are also disclosed.

U.S. Pat. No. 4,659,337 discloses the use of the reaction product of maleic anhydride, a polyether polyamide containing oxyethylene and oxypropylene ether moieties, and a hydrocarbyl polyamine in a gasoline motor fuel to reduce engine ORI and provide carburetor detergency.

U.S. Pat. No. 4,659,336 discloses the use of the mixture of (i) the reaction product of maleic anhydride, a polyether polyamine containing oxyethylene and oxypropylene ether moieties and a hydrocarbyl polyamine, and (ii) a polyolefin polymer/copolymer as an additive in motor fuel compositions to reduce engine ORI.

U S. Pat. No. 4,631,069 discloses an alcohol-containing motor fuel composition which additionally comprises an anti-wear additive which is the reaction product of a dibasic acid anhydride, a polyoxyisopropylene diamine of the formula:

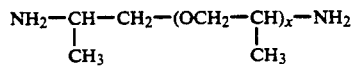

where x has a value of 2-68, and an N-alkyl-alkylene diamine.

U.S. Pat. No. 4,643,738 discloses a motor fuel composition comprising a deposit-control additive which is the reaction product of a dibasic acid anhydride, a polyoxyisopropylene diamine of the formula:

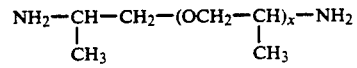

where x has a value of 2-50, and an N-alkyl-alkylene diamine.

U.S. Pat. No. 4,604,103 discloses a motor fuel deposit control additive for use in internal combustion engines which maintains cleanliness of the engine intake system without contributing to combustion chamber deposits or engine ORI. The additive disclosed is a hydrocarbyl polyoxyalkylene polyethylene amine of molecular weight range 300-2,500 having the formula:

$$R-(OCH_2CH)_x-OCH_2CH_2-NR''R'''$$
$$\phantom{R-(OCH_2}|\phantom{H)_x-OCH_2CH_2-NR''R'''}$$
$$\phantom{R-(OCH_2CH)_x-}R'$$

where R is a hydrocarbyl radical of from 1 to about 30 carbon atoms; R' is selected from methyl and ethyl; x is an integer from 5 to 30, and R" and R''' are independently selected from hydrogen and —(CH$_2$CH$_2$N-H)y—H, where y is an integer from 0 to 5.

U.S. Pat. No. 4,581,040 discloses the use of a reaction product as a deposit-inhibitor additive in fuel compositions. The reaction product is the condensation product of the process comprising (i) reacting a dibasic acid anhydride with a polyoxyisopropylene diamine of the formula:

$$NH_2-CH-CH_2-(OCH_2-CH)_x-NH_2$$
$$\phantom{NH_2-}|\phantom{CH-CH_2-(OCH_2-}|$$
$$\phantom{NH_2-}CH_3\phantom{-CH_2-(OCH_2-}CH_3$$

where x is a numeral of about 2-50, thereby forming a bismaleamic acid; (ii) reacting said maleamic acid with a polyalkylene polyamine, thereby forming a condensate product; and (iii) recovering said condensate product.

Co-pending U.S. patent application Ser. No. 07/896,700 discloses alkylphenoxypolyoxyalkylene amidoalkanolamines.

U.S. Pat. No. 4,357,148 discloses a motor fuel additive useful in controlling ORI which is the combination of (a) an oil-soluble aliphatic polyamine containing at least one olefinic polymer chain, and (b) a polymer, copolymer, or corresponding hydrogenated polymer or copolymer of a C$_2$-C$_6$ mono-olefin with a molecular weight of 500-1,500.

U.S. Pat. No. 4,234,321 discloses a hydrocarbyl-poly(oxyalkylene) ureylene carbamate as a deposit control additive for fuels.

EP 297996 discloses an alkylphenylpoly(oxypropylene) aminocarbamate having a molecular weight ranging from 600 to 6000 for use in gasoline or diesel fuel compositions.

SUMMARY OF THE INVENTION

The present invention provides a novel class of compounds, useful as gasoline detergent additives, of polyether hydroxyethylaminoethyloxalamides represented by the formula:

The present invention also provides a motor fuel composition comprising:

(a) a major portion of a hydrocarbon fuel boiling in the range between 90° F. and 370° F.; and (b) a minor amount, sufficient to reduce the formation of deposits on intake valves, of a polyetheramine as shown above in formula (I).

A method of synthesizing the polyetheramines of the present invention is also provided.

DETAILED DESCRIPTION OF THE INVENTION

Applicants' have discovered a new class of polyetheramines which are useful as detergents in motor fuel compositions. These polyetheramines detergents are more efficacious in removing and preventing the build up of deposits on intake valves than some commercially available detergent packages. In addition, the polyether hydroxyethylaminoethyloxalamides motor fuel additives of the present invention will not contribute significantly, if at all, to octane requirement increase, a problem which confronts all gasoline spark ignition engines.

The polyether hydroxyethylaminoethyloxalamides of the present invention are represented by the formula:

$$R-\underset{}{\bigcirc}-O(CH_2-\underset{\underset{H}{|}}{\overset{\overset{CH_3}{|}}{C}}-O)_n CH_2-\underset{\underset{H}{|}}{\overset{\overset{CH_3}{|}}{C}}-\underset{\underset{H}{|}}{N}-$$

$$-\overset{\overset{O}{\|}}{C}-\overset{\overset{O}{\|}}{C}-NH-CH_2CH_2\underset{\underset{H}{|}}{N}CH_2CH_2OH$$

wherein R is a (C$_5$-C$_{25}$) alkyl group and n is an integer between about 5 and about 20.

Preferably, R is a (C$_9$-C$_{21}$) alkyl group, and n is an integer between about 9 and about 15. In another preferred embodiment, R is a (C$_{12}$-C$_{21}$) alkyl group and n is an integer between about 9 and about 15. Most preferably, R is a nonyl qroup, and n has an average value of 12.5.

Also, according to the present invention, the phenyl ring can contain a second nonyl substituent. In such cases the first nonyl group would be in the para position and the second nonyl group would be in the ortho position to the remainder of the molecule.

Synthesis of Polyetheramine

The preparation of the polyether hydroxyethylaminoethyl oxalamides of the present invention is illustrated by the reaction of a hydrocarbyloxypolyoxyalkylene amine (polyetheramine) with diethyloxalate and aminoethylethanolamine where R is a (C$_5$ H$_{25}$) alkyl group and n is an integer between about 5 and about 20:

$$R-\underset{}{\bigcirc}-O\left(CH_2-\underset{\underset{H}{|}}{\overset{\overset{CH_3}{|}}{C}}-O\right)_n CH_2-\underset{\underset{H}{|}}{\overset{\overset{CH_3}{|}}{C}}-\underset{\underset{H}{|}}{N}-\overset{\overset{O}{\|}}{C}-\overset{\overset{O}{\|}}{C}-NH-CH_2CH_2\underset{\underset{H}{|}}{N}CH_2CH_2OH \qquad (I)$$

where R is a (C$_9$-C$_{25}$) alkyl group and n is an integer between about 5 to 20.

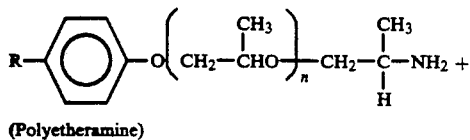

(Polyetheramine)

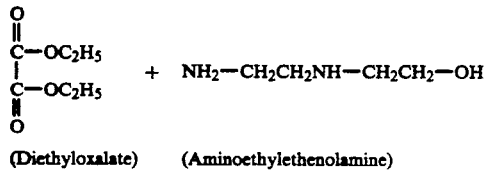

(Diethyloxalate)     (Aminoethylethenolamine)

The most preferred polyetheramine, nonylphenoxypolyoxypropyleneamine is represented by the formula

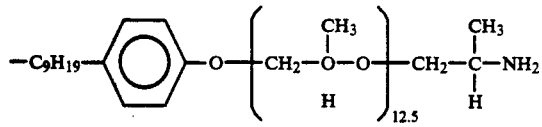

It should be noted that the polyetheramines useful in the present invention generally have one, but in some instances, two nonyl groups substituted onto the phenyl ring. In fact, it is likely that available contains at least some of the di-nonyl substituted phenyl ring versions of this compound. In such cases, the second nonyl group is located in the ortho position relative to the bulk of the molecule.

The Motor Fuel Composition

The motor fuel composition of the present invention comprises a major portion of a hydrocarbon fuel boiling in the gasoline range between 90° F. and about 370° F., and a minor portion of the allophonate ester additive of the present invention sufficient to reduce the formation of deposits on intake valves.

Preferred base motor fuel compositions are those intended for use in spark ignition internal combustion engines. Such motor fuel compositions, generally referred to as gasoline base stocks, preferably comprise a mixture of hydrocarbons boiling in the gasoline boiling range, preferably from about 90° F. to about 370° F. This base fuel may consist of straight chain or branched chain paraffins, cycloparaffins, olefins, aromatic hydrocarbons, or mixtures thereof. The base fuel can be derived from, among others, straight run naphtha, polymer gasoline natural gasoline, or from catalytically cracked or thermally cracked hydrocarbons and catalytically reformed stock. The composition and octane level of the base fuel are not critical and any conventional motor fuel base can be employed in the practice of this invention. In addition, the motor fuel composition may contain any of the additives generally employed in gasoline. Thus, the fuel composition can contain anti-knock compounds such as tetraethyl lead compounds, anti-icing additives, and the like.

In a broad embodiment of the fuel composition of the present invention, the concentration of the additive is about 25 to about 175 PTB (pounds per thousand barrels of gasoline base stock). In a preferred embodiment, the concentration of the additive composition is about 50 to about 150 PTB. In a more preferred embodiment, the concentration of the additive composition is about 75-125 PTB.

The additive of the present invention can also be used effectively with heavy oils such as SNO-600, SNO-850, etc., or with synthetics such as polypropylene glycol (1000 m.w.) at concentrations of 30-100 PTB, and 75-125 PTB in particular.

The additive of the present invention is effective in very small concentrations, and therefore, for consumer end use it is desirable to package it in dilute form. Thus, a dilute form of the additive composition of the present invention can be provided comprising a diluent e.g., xylene and about 1 to about 50 wt. % of the additive.

The preparation and advantages of the polyetheramines of the present invention are further illustrated by the following Examples.

EXAMPLE I

Preparation of Polyether Hydroxyethylaminoethyl Oxalamide

To a three liter three-necked flask equipped with a Dean-Stark trap, thermometer, stirrer and nitrogen outlet was charged 800 g of nonylphenoxypolyoxypropyleneamine (aminated 13.5 mole propylene oxide adduct of nonylphenol) and 370 grams of diethyloxalate. The mixture was heated to 50° C. for one hour and then 120° C. for two hours. Ethanol was removed through the Dean-Stark trap. The resulting mixture was placed under a vacuum and heated to 120° C. to remove the unreacted diethyloxalate and the remaining ethanol. About 851 g of the resulting oxalate adduct and 85 g of aminoethylethanolamine were mixed and heated to 130° C. for two hours. Xylene (620 g) was then added to the final product (60% active form). This material is shown as product I where n=12.5 and R is nonyl.

Honda Generator Test

A test was developed to determine the intake valve detergency of an additive as well as to determine whether the additive will cause the intake valves to stick.

In small four-cylinder gasoline powered engines, the intake valves accumulate large amounts of deposits which interfere with the operation of the engine. A good detergent/dispersant is required to prevent the buildup of these deposits. The Honda Generator test was developed to measure the activity of additives in preventing the buildup of intake valve deposits (IVD) (keep clean). The measurements are done in two ways: (1) the intake valves at the end of the run are rated using the CRC method of rating (a valve with a rating of 10 is perfectly clean, and a valve rating of 6 or less denotes heavy deposit levels); and (2) intake valve deposit weights are obtained and also reported in grams.

HONDA GENERATOR

Test Equipment

The Intake System Deposit/Intake Valve Stickiness Test consists of an electrical generator driven by a current technology gasoline engine, similar in many characteristics to modern vehicle engines. The generator set design allows the engine to be easily loaded by using the electrical generator as a dynamometer for the engine. The set operates at a governed speed of 3600 rpm and incorporates a twin cylinder, overhead camshaft, water-cooled engine described below in Table I.

TABLE I

| Engine Data for ES6500 Honda Generator | |
|---|---|
| Type: 4-stroke | Overhead cam, 2 cylinder |
| Cooling System: | Liquid cooled |
| Displacement: | 359 cc |
| Bore × Stroke: | 58 × 68 mm |
| Construction: | Aluminum head and block, fixed cast iron cylinder liners |
| Compression: | 8.5:1 |
| Maximum Power: | 9.1 Kw/3600 rpm |
| Maximum Torque: | 240 kg-cm |
| Fuel System: | Carburetor |
| Recommended Fuel: | Unleaded gasoline with min 86 (R + M)/2 octane |

The results of these tests are set forth below in Table II, which were obtained for "keep Clean" activity.

TABLE II

| Honda Test Results | | |
|---|---|---|
| | Test Fuel | Petrox |
| CRC Valve Rating[1] | 9.3 | 6.03 |
| IVD Weight, grm | 0.007 | 0.269 |
| Stickiness | No | No |

The test fuel contained 100 PTB of the subject polyether hydroxyethylaminoethyl oxalamide solution and 100 PTB of heavy oil. It gave excellent CRC valve ratings (9.3), virtually no deposits on the intake valves (7 mg or less) and exhibited no stickiness. Petrox is a commercially available additive package. At 60 PTB it showed a poor CRC rating and gave 269 mg IVD deposits. Petrox did not demonstrate valve stickiness.

THERMAL GRAVEMETIC ANALYSIS (TGA)

TGA is used herein to establish the uniqueness of the polypropylene polyethers of the present invention.

Accordingly, a sample of the present additives was analyzed for rate of thermal decomposition using thermal gravimetric analysis (TGA). Specific procedure is the Chevron test method which involves heating of materials in air at a rapid rate and measuring volatility of materials at 200° C. and 295° C. The following results were obtained at the different temperatures for the polyetherpropane diamine described above.

| Temperature | % Volatilized (in Air) |
|---|---|
| 200° C. | 5 to 10 |
| 295° C. | 80 to 90 |

Thus, at 295° C., 80 to 90 percent of the additive had thermally decomposed and volatilized. This indicates that the additive should leave only small amounts of combustion chamber deposits during actual engine operation.

We claim:

1. A polyether hydroxyethylaminoethyl oxalamide detergent/dispersant represented by the formula $$R-\phenyl-O+CH_2-\underset{H}{\overset{CH_3}{C}}-O)_n CH_2-\underset{H}{\overset{CH_3}{C}}-\underset{H}{N}-$$

$$-\overset{O}{\underset{}{C}}-\overset{O}{\underset{}{C}}-NH-CH_2CH_2\underset{H}{N}CH_2CH_2OH$$

wherein R is a ($C_5$–$C_{25}$) alkyl group and n is an integer between about 5 and about 20.

2. The polyether hydroxyethylaminoethyl oxalamide of claim 1 where R is a ($C_9$–$C_{21}$) alkyl group, and n is an integer between about 9 and about 15.

3. The polyether hydroxyethylaminoethyl oxalamide of claim 1 where R is a ($C_{12}$–$C_{21}$) alkyl group and n is an integer between about 9 and about 15.

4. A motor fuel composition comprising:
   (a) a major portion of a hydrocarbon fuel boiling in the range between 90° F. and 370° F.; and
   (b) a minor amount, sufficient to reduce the formation of deposits on intake valves, of a polyether hydroxyethylaminoethyl oxalamide of the formula $$R-\phenyl-O+CH_2-\underset{H}{\overset{CH_3}{C}}-O)_n CH_2-\underset{H}{\overset{CH_3}{C}}-\underset{H}{N}-$$

$$-\overset{O}{\underset{}{C}}-\overset{O}{\underset{}{C}}-NH-CH_2CH_2\underset{H}{N}CH_2CH_2OH$$

where R is nonyl ($C_9 H_{19}$) and is integer of 12.5.

5. The motor fuel composition of claim 4 wherein the polyether hydroxyethylaminoethyl oxalamide is present in an amount of between about 25 and about 125 PTB.

6. The motor fuel composition of claim 4 wherein the polyther hydroethylaminoethyl oxalamide is present in an amount of between about 75 and about 125 PTB.

7. The motor fuel composition of claim 4 wherein the polyether hydroxyethylaminoethyl oxalamide is present in an amount of about 100 PTB.

* * * * *